United States Patent [19]

Hermolin et al.

[11] Patent Number: 5,340,445
[45] Date of Patent: Aug. 23, 1994

[54] PROCESS FOR THE PURIFICATION OF DIAMINODIPHENYL COMPOUNDS

[75] Inventors: Joshua Hermolin, Ramat Hasharon; Hugo Keselman, Karmiel; Jacob Oren, Qiryat Bialik, all of Israel

[73] Assignee: Bromine Compounds Ltd., Beer-Sheva, Israel

[21] Appl. No.: 896,833

[22] Filed: Jun. 11, 1992

[30] Foreign Application Priority Data

Jun. 16, 1991 [IL] Israel .......................... 98520

[51] Int. Cl.$^5$ .......................... B01D 3/10; B01D 3/34
[52] U.S. Cl. .......................... 203/33; 203/37; 203/91; 564/437
[58] Field of Search .......................... 203/33, 91, 36, 37, 203/DIG. 6; 564/437

[56] References Cited

U.S. PATENT DOCUMENTS

| | | | |
|---|---|---|---|
| 4,189,354 | 2/1980 | Ellendt et al. | 203/81 |
| 4,404,063 | 9/1983 | Honda | 203/33 |
| 4,454,347 | 6/1984 | Parham et al. | |
| 4,700,011 | 10/1987 | Pillsbury | 568/585 |
| 4,825,002 | 4/1989 | Davis | 564/437 |
| 5,019,653 | 5/1991 | Speranza et al. | |

FOREIGN PATENT DOCUMENTS

| | | | |
|---|---|---|---|
| 0697087 | 11/1964 | Canada | 564/437 |
| 0732244 | 4/1966 | Canada | 568/585 |
| 0041837 | 12/1981 | European Pat. Off. | 564/437 |
| 0094212 | 11/1983 | European Pat. Off. | |
| 45-4737 | 2/1970 | Japan | 564/437 |
| 4935341 | 7/1972 | Japan | 564/437 |
| 0146850 | 8/1985 | Japan | 564/437 |
| 0199861 | 10/1985 | Japan | 564/437 |
| 1136637 | 12/1968 | United Kingdom | 568/585 |
| 1377677 | 12/1974 | United Kingdom | 568/585 |

OTHER PUBLICATIONS

Patent Abstracts of Japan 14, No. 37 (C-680) 1989 Mitsui Petrochem Ind. Ltd.
Patent Abstracts of Japan 11, No. 60 (C-405) 1985 Mitsui Toatsu Chem. Inc.

*Primary Examiner*—Virginia Manoharan
*Attorney, Agent, or Firm*—Michael N. Meller

[57] ABSTRACT

Diaminodiphenyl-compounds of the structure selected from:

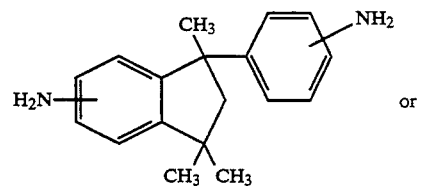

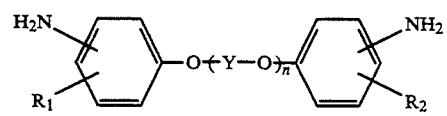

wherein
$R_1$ and $R_2$ can be: H, —$CH_3$, —$C_2H_5$, —$C_3H_7$, —$C_4H_9$ or

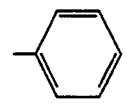

Y can be: $C(CH_3)_2$,

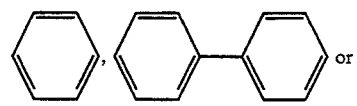

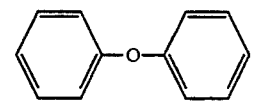

n=0; 1.

are purified by distilling the crude product obtained under vacuum in one step, in the presence of one or more alkaline bases.

9 Claims, No Drawings

PROCESS FOR THE PURIFICATION OF DIAMINODIPHENYL COMPOUNDS

FIELD OF THE INVENTION

The present invention relates to the purification of diaminodiphenyl-compounds by fractional distillation in the presence of alkaline bases.

BACKGROUND OF THE INVENTION

The Prior Art

Aromatic diamino compounds are well known as building blocks for high performance polymers (polyamides, polyimides, etc.), antioxidants, intermediates for dyestuffs and a variety of other applications. However, the production of the diaminodiphenyl compounds leads, in most cases, to considerable amounts of side products as a result of side reactions and degradation under the production conditions.

The diaminodiphenyl compounds to which the present invention is directed are selected from:

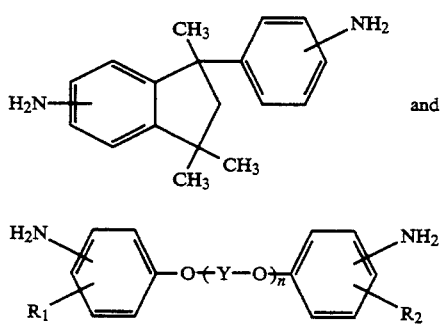

wherein
$R_1$ and $R_2$ can be: H, $-CH_3$, $-C_2H_5$, $-C_3H_7$, $-C_4H_9$ or

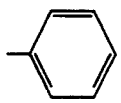

Y can be: $C(CH_3)_2$,

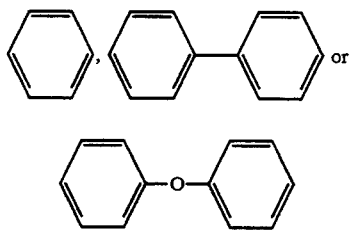

n=0;1.

The purification of diaminodiphenyl ethers is described in detail in JP 01,272,558. In this patent crude 3,4'-diaminodiphenyl ether (3,4'-DADPE) is purified by carrying out two consecutive distillations: a first, rough distillation to remove the heavy and high boiling materials, followed by a second, fine distillation.

It is claimed that this process leads to purification in high yields and in the high purity which is necessary for certain polymers. However, this is achieved by a double distillation and the use of large distillation columns, which lead to undue operational and economic drawbacks.

The patent gives an example of 30 theoretical plates to distill 3,4'-diaminodiphenyl ether in 99.99% purity. Moreover, when operating according to the process disclosed in JP 01,272,558 some additional technical problems arise in the first rough distillation, e.g. the heavy residues are removed from the distillation system with great difficulty, as they are highly viscous and insoluble in organic or aqueous solvents.

In the above patent, the prior art is critically discussed in detail:

Recrystallization of diaminodiphenyl ether is disclosed in U.S. Pat. No. 4,539,428 and JP 61,221,157. However, such an operation is expensive and troublesome, and the yields of the recovered products and solvents are relatively low.

Conversion into dihydrochloride salts followed by neutralization is disclosed in U.S. Pat. No. 1,890,256 and in JP 61,225,155. However, this operation is associated with large amounts of waste (2 equivalents of salts, such as $NH_4Cl$, per one mole of product).

Different approaches are revealed in the following two patents:

a) distillation and fast cooling of diaminodiphenyl ether in JP 61,05,056, which is criticized in JP 01,272,558 as being insufficient to achieve the high purity that is required for high performance polymers. The need to quickly cool the distillate according to this process suggests that, indeed, it still contains impurities that darken the product at the elevated temperature; and b) distillation in the presence of an inert organic solvent in JP 61,221,159, which leads to unnecessary solvent losses and/or to the need for additional facilities to separate and recycle the solvent.

SUMMARY OF THE INVENTION

We have now surprisingly found, and this is an object of the invention, that crude diaminodiphenyl-compounds can be purified in high yield and high purity by distillation in one step if alkali bases like NaOH and/or KOH are present. Accordingly, the requirements for fast operation and/or columns of high performance are less rigorous, the degradation of the diaminodiphenyl-compounds is much slower and the color of the pure product is better. Naturally, these results lead to significant economic advantages over prior art processes:

a. The fractional distillation of the diaminodiphenyl-compounds can be carried out in one step, as a result of the substantial reduction in the decomposition of the compounds in the reboiler.

b. The distillation range of temperatures and pressures is significantly higher (based on the concentration of the corresponding diaminodiphenyl-compound in the crude material) and the purity of the distilled product is considerably higher even if the distillation is conducted under less exacting conditions and using less efficient columns (i.e. smaller number of theoretical plates). In fact, in some cases, i.e., when the product is very sensitive, the fractional distillation method of purification is not economically viable unless NaOH or KOH are used.

c. The distilled product is completely stable and does not darken on storage for long periods (1 year). and d. The high boiling residue after the distillation is easily washed off by dissolving it in water.

The diaminodiphenyl-compounds that can be purified according to the invention are those which melt and can be distilled under vacuum at a temperature range $\leq 400°$ C. The vacuum should be as high as possible to operate at the lowest temperature possible, but the operating temperature should not be below the melting point of the respective diaminodiphenyl-compound which may lead to sublimation. On the other hand, the high vacuum should not itself impose an undue economic burden because of too expensive pumping systems. The range of vacuum that is most suitable from an industrial point of view is 0.1–400 mm Hg. As the diaminodiphenyl-compounds are very sensitive to oxygen, efforts should be made to exclude it as much as possible.

It is another object of the invention to provide diaminodiphenyl-compounds of improved quality and properties, such as less discoloration and longer shelf life.

Compounds of the following structures are included:

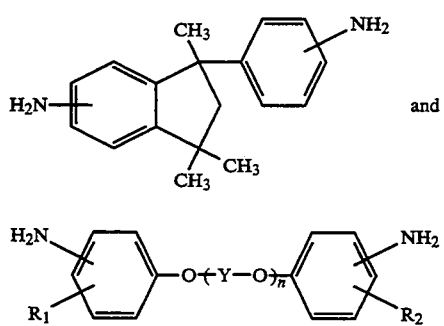

and

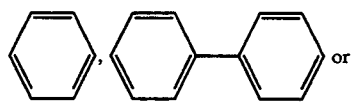

wherein $R_1$ and $R_2$ can be: H, —CH$_3$, —C$_2$H$_5$, —C$_3$H$_7$, —C$_4$H$_9$ or

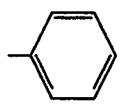

Y can be: C(CH$_3$)$_2$,

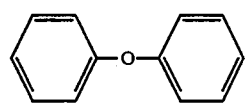

or

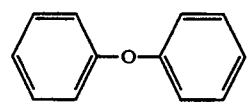

$n=0$; 1.

Alkali bases have a surprising effect on the behavior of most of the diaminodiphenyl-compounds. They do not cleave the diaminodiphenyl-compound at the high temperatures at which the distillation is carried out. On the contrary, for reasons which are not at all clear, the addition of the alkali bases improves the stability of the crude materials as is demonstrated by the examples.

All alkali bases are effective for the above purpose, but the most economic and efficient ones are those based on Na$^+$ (like Na$_2$O, NaOH, NaHCO$_3$, Na$_2$CO$_3$). Similar compounds of Li$^+$ and K$^+$ can also be used, although they are somewhat more expensive. Bases derived from divalent and trivalent ions like Ca$^{++}$, Mg$^{++}$, Al$^{+++}$ can also be used, but they are somewhat less effective. When using carbonates under the distillation conditions, the CO$_3^{-2}$ is decomposed leaving the corresponding base in the system.

The amount of the base should be such that it is sufficient to react with all the acidic moieties which are introduced into the distillation system or formed during this operation, but it is by no means necessary to maintain stoichiometric quantities of the base.

As a preferred embodiment, the present invention provides a process for the purification of a crude diaminodiphenyl compound of the structure

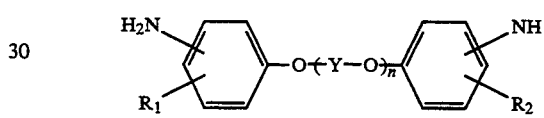

wherein $R_1$ and $R_2$ are each H, CH$_3$, C$_2$H$_5$, C$_3$H$_7$, C$_4$H$_9$ or

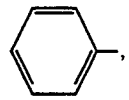

Y is C(CH$_3$)$_2$,

and $n=0$ or 1 in which the crude product is distilled under vacuum in one step in the presence of at least one alkaline metal base, wherein the distillation temperature is in the range between the melting point of the respective diaminodiphenyl compound and about 400° C., the pressure is in the range 0.1–400 mm Hg and is maintained at a level at which sublimation of the diaminodiphenyl compound does not occur, and wherein distillation is carried out in the substantial absence of oxygen or ambient air.

DETAILED DESCRIPTION OF THE INVENTION

EXAMPLE 1

Amination of 4,4'-dibromo-diphenyl-ether (DBDPE)

Amination carried out as described in U.S. Pat. No. 1,890,256, as follows:

Into a 100 liter SS-316 autoclave there were placed DBDPE (16.41 Kg, 50 moles), aqueous 25% $NH_3$ (50 l, 65 moles) and $CuSO_4.5H_2O$ (2.5 Kg, 10 mole). The autoclave was sealed and heated to 190° C. with rapid stirring (250 rpm). The progress of the reaction and its completion were followed by means of a graph of the internal pressure of the autoclave versus time and, at the end of the reaction, by analysis of the bromine ion. After four hours, the autoclave was cooled to room temperature, the pressure was released and the autoclave was opened. The reaction mixture was filtered and washed with aqueous 25% $NH_3$ (20 l) and with water (50 l).

The crude DADPE (9.3 Kg; Ia) was obtained after drying under vacuum (~30 mm Hg) at 80° C. The purity of the sample was analyzed by HPLC (High performance liquid chromatography), DSC (Differential scanning calorimetry) and AA (Atomic absorption) analyses, the results of which are summarized in Table 1. The sample was split into portions for further tests, as follows:

EXAMPLE 1A

Recrystallization in Acetonitrile

The crude DADPE (200 g; Ia) was dissolved in acetonitrile (1400 ml) at 75° C. The solution was cooled to 20° C. and the crystals of DADPE were filtered and dried under vacuum (~1 mm Hg) at 100° C. The dry DADPE (164 g; Ib) sample was analyzed—see Table 1.

The above recrystallization procedure was repeated using the purified product (80 g; Ib). The dry DADPE (63 g; Ic) sample was analyzed. See Table 1.

The above recrystallization procedure was repeated using the purified product (80 g; Ib) and active carbon (16 g). The dry DADPE (60 g; Id) sample was analyzed. See Table 1.

EXAMPLE 1B

Distillation of the Crude DADPE—Stability Tests

A sample of the crude DADPE (100 g; Ia) and varying amounts and types of ground bases were introduced into a flask. It was then evacuated and maintained under the specified vacuum during the experiment. The flask was heated to 250° C. for the specified time, then cooled to ambient temperature and analyzed—see Table 2.

EXAMPLE 1C

Distillation of the Crude DADPE

A sample of the crude DADPE (100 g; Ia) and varying amounts of ground bases were introduced into a distillation system. It was then evacuated and maintained under the specified temperature and vacuum conditions during the experiment. Fractions of the distilled product were collected and analyzed at the end of the distillation (after cooling completely to ambient temperature)—see Table 3.

TABLE 1

| Recrystallization The Compound: 4,4'-diaminodiphenylether (4,4'-DADPE) | | | | |
| --- | --- | --- | --- | --- |
|  | Ia | Ib | Ic | Id |
| HPLC (Calibrated) 4,4'-DADPE (% wt) | 95.0 | 98.5 | 99.2 | 99.5 |
| DSC 4,4'-DADPE (% wt) | — | 98.9 | 99.4 | 99.6 |
| A.A. | | | | |
| Cu (ppm) | 112 | 49 | 21 | 5 |
| Fe (ppm) | 39 | 43 | 45 | 8 |

TABLE 2

| Stability test The Compound: 4,4'-diaminodiphenylether (4,4'-DADPE) | | | | | | | | |
| --- | --- | --- | --- | --- | --- | --- | --- | --- |
| | | Base | Temp. | Vacuum | 4,4'-DADPE (% by HPLC) | | | |
| Sample | Type | Weight g | °C. | mm Hg | 0 hrs | 1 hr | 4 hrs | 8 hrs |
| Ia | — | — | 25 | 760 | 95.0 | 95.0 | 95.0 | 95.0 |
| Ia-1 | — | — | 250 | 15–25 | 95.0 | 90.4 | 87.3 | 82.5 |
| Ia-2 | NaOH | 3 | 250 | 15–25 | 95.0 | 95.1 | 94.8 | 94.9 |
| Ia-3 | KOH | 4 | 250 | 15–25 | 95.0 | 94.8 | 94.9 | 94.7 |
| Ia-4 | $Ca(OH)_2$ | 3 | 250 | 15–25 | 95.0 | 94.1 | 93.8 | 93.2 |
| Ia-5 | $Mg(OH)_2$ | 3 | 250 | 15–25 | 95.0 | 92.2 | 90.3 | 89.2 |
| Ia-6 | $Al(OH)_2$ | 3 | 250 | 15–25 | 95.0 | 91.7 | 89.4 | 89.1 |
| Ia-7 | $Na_2CO_3$ | 4 | 250 | 15–25 | 95.0 | 94.9 | 95.1 | 94.8 |
| Ia-8 | $K_2CO_3$ | 5 | 250 | 15–25 | 95.0 | 94.7 | 94.7 | 94.8 |

TABLE 3

| Distillation The Compound: 4,4'-diaminodiphenylether (4,4'-DADPE) | | | | | | | | | |
| --- | --- | --- | --- | --- | --- | --- | --- | --- | --- |
| | | | | Theor. | | 4,4'-DADPE (%) | | Metals (ppm) | |
| Sample | Type of base | Temp. °C. | Vacuum mm Hg | Plates # | Yld. % | HPLC | DSC | Cu | Fe | Other |
| Ia-9 | — | 245 ± 5 | 10–20 | 1 | 82 | 97.5 | — | <0.5 | <0.5 | |
| Ia-10 | — | 245 ± 5 | 10–20 | 5 | 77 | 98.5 | 98.5 | <0.5 | <0.5 | |
| Ia-11 | NaOH 2% | 245 ± 5 | 15–25 | 1 | 98 | 99.2 | 99.4 | <0.5 | <0.5 | <1.0 Na |
| Ia-12 | NaOH 2% | 250 ± 5 | 10–20 | 5 | 95 | 99.5 | 99.7 | <0.5 | <0.5 | <1.0 Na |
| Ia-13 | NaOH 2% | 255 ± 5 | 10–20 | 10 | 95 | 99.9 | 99.96 | <0.5 | <0.5 | <1.0 Na |

TABLE 3-continued

Distillation
The Compound: 4,4'-diaminodiphenylether (4,4'-DADPE)

| Sample | Type of base | Temp. °C. | Vacuum mm Hg | Theor. Plates # | Yld. % | 4,4'-DADPE (%) | | Metals (ppm) | | |
|---|---|---|---|---|---|---|---|---|---|---|
| | | | | | | HPLC | DSC | Cu | Fe | Other |
| Ia-14 | NaOH 2% | 255 ± 5 | 10–20 | 20 | 97 | 99.9 | 99.99 | <0.5 | <0.5 | <1.0 Na |
| Ia-15 | KOH 3% | 250 ± 5 | 10–20 | 1 | 97 | 99.2 | 99.5 | <0.5 | <0.5 | <1.0 K |
| Ia-16 | KOH 3% | 250 ± 5 | 10–20 | 10 | 95 | 99.9 | 99.96 | <0.5 | <0.5 | <1.0 K |

Both the advantages of distillation vis-a-vis recrystallization and the presence of bases in the distillation system are clearly demonstrated in these tables.

EXAMPLE 2

Amination of 4,4'-dibromo-3-methyldiphenyl ether (DBMDPE)

Amination described in Example 1 was repeated using DBMDPE. The Crude DAMDPE (5.32 Kg; 11a) was obtained after drying under vacuum (~30 mm Hg) at 80° C. The purity of the sample was determined by HPLC (High performance liquid chromatography), DSC (Differential scanning calorimetry) and AA (Atomic absorption) analyses, the results of which are summarized in Table 4. The sample was split into portions for further tests as follows:

TABLE 4

Recrystallization
The Compound:
4,4'-diamino-3-methyl-diphenylether (4,4'-DAMDPE)

| | IIa | IIb | IIc | IId |
|---|---|---|---|---|
| HPLC (Calibrated) 4,4'-DAMDPE (% wt) | 89.0 | 95.5 | 98.2 | 98.5 |
| DSC 4,4'-DAMDPE (% wt) | — | — | 98.5 | 98.7 |
| A.A. | | | | |
| Cu (ppm) | 500 | 50 | 20 | 15 |
| Fe (ppm) | 30 | 35 | 38 | 10 |

EXAMPLE 2a

Recrystallization in Acetonitrile

The crude DAMDPE (200 g; 11a) was dissolved in acetonitrile (400 ml) at 75° C. The solution was cooled to 20° C. and the crystals of DAMDPE were filtered and dried under vacuum (~1 mm Hg) at 100° C. The dry DAMDPE (128 g; 11b) sample was analyzed—see Table 4.

The above recrystallization procedure was repeated using the purified product (60 g; 11b). The dry DAMDPE (45 g; 11c) sample was analyzed; see Table 4.

The above recrystallization procedure was repeated using the purified product (60 g; 11b) and active carbon (6 g). The dry DAMDPE (42.5 g; 11d) sample was analyzed; see Table 4.

EXAMPLE 2b

Distillation of the Crude DAMDPE—Stability Tests

A sample of the crude DAMDPE (100 g; 11a) and varying amounts and types of ground bases were introduced into a flask. It was then evacuated and maintained under the specified vacuum during the experiment. The flask was heated to 280° C. for the specified time, then cooled to ambient temperature and analyzed—see Table 5.

TABLE 5

Stability test
The Compound: 4,4'-diamino-3-methyl-diphenylether (4,4'-DAMDPE)

| | Base | | | Vacuum | 4,4'-DADPE (% by HPLC) | | | |
|---|---|---|---|---|---|---|---|---|
| Sample | Type | Weight g | Temp. °C. | mm Hg | 0 hrs | 1 hr | 4 hrs | 8 hrs |
| IIa | — | — | 25 | 760 | 89.0 | 89.0 | 89.0 | — |
| IIa-1 | — | — | 280 | 30–40 | 89.0 | 78.3 | 62.1 | — |
| IIa-2 | NaOH | 3 | 280 | 30–40 | 89.0 | 88.2 | 89.0 | — |
| IIa-3 | KOH | 4 | 280 | 30–40 | 89.0 | 88.6 | 88.9 | — |

EXAMPLE 2c

Distillation of the Crude DAMDPE

A sample of the crude DAMDPE (100 g; IIa) and varying amounts of ground bases were introduced into a distillation system. It was then evacuated and maintained under the specified temperature and vacuum conditions during the experiment. Fractions of the distilled product were collected and analyzed at the end of the distillation (after cooling completely to ambient temperature )—see Table 6.

TABLE 6

Distillation
The Compound: 4,4'-diamino-3-methyl-diphenylether (4,4'-DAMDPE)

| Sample | Type of base | Temp. °C. | Vacuum mm Hg | Theor. Plates # | Yld. % | 4,4'-DADPE (%) | | Metals (ppm) | | |
|---|---|---|---|---|---|---|---|---|---|---|
| | | | | | | HPLC | DSC | Cu | Fe | Other |
| IIa-4 | — | 230 ± 5 | 5 | 1 | 80 | 95.0 | — | <0.5 | <0.5 | |
| IIa-5 | — | 230 ± 5 | 5 | 5 | 75 | 97.0 | — | <0.5 | <0.5 | |
| IIa-6 | NaOH 4% | 230 ± 5 | 5 | 1 | 90 | 98.0 | 98.7 | <0.5 | <0.5 | <1.0 Na |
| IIa-7 | NaOH 4% | 230 ± 5 | 5 | 5 | 93 | 99.0 | 98.9 | <0.5 | <0.5 | <1.0 Na |
| IIa-8 | NaOH 4% | 230 ± 5 | 10–20 | 10 | 93 | 99.5 | 99.8 | <0.5 | <0.5 | <1.0 Na |
| IIa-9 | NaOH 4% | 230 ± 5 | 10–20 | 20 | 95 | 99.5 | 99.9 | <0.5 | <0.5 | <1.0 Na |

TABLE 6-continued

Distillation
The Compound: 4,4'-diamino-3-methyl-diphenylether (4,4'-DAMDPE)

| Sample | Type of base | Temp. °C. | Vacuum mm Hg | Theor. # | Yld. % | 4,4'-DADPE (%) | | Metals (ppm) | | |
|---|---|---|---|---|---|---|---|---|---|---|
| | | | | | | HPLC | DSC | Cu | Fe | Other |
| IIa-10 | KOH 3% | 230 ± 5 | 10–20 | 1 | 97 | 99.3 | 99.1 | <0.5 | <0.5 | <1.0 K |
| IIa-11 | KOH 4% | 250 ± 5 | 10–20 | 10 | 95 | 99.9 | 99.9 | <0.5 | <0.5 | <1.0 K |

EXAMPLE 3

Amination of 1,4-Bis(4-bromophenoxy) benzene (DBTPE)

The amination described in Example 1 was repeated using DBTPE. The crude 1,4-Bis-(4-aminophenoxy)-benzene (DATPE) (6.2 Kg: IIIa) obtained after drying under vacuum (~30 mm Hg) at 80° C. The purity of the sample was analyzed by HPLC (High performance liquid chromatography), DSC (Differential scanning calorimetry) and AA (Atomic absorption) analyses, the results of which are summarized in Table 7. The sample was split into portions for further tests as follows:

TABLE 7

Recrystallization
The Compound: 1,4-Bis(4-aminophenoxy)-benzene (DATPE

| | IIIa | IIIb | IIIc | IIId |
|---|---|---|---|---|
| HPLC (Calibrated) DATPE (% wt) | 89.0 | 95.5 | 98.2 | 98.5 |
| DSC DATPE (% wt) | — | — | 98.5 | 98.7 |
| A.A. | | | | |
| Cu (ppm) | 760 | 66 | 32 | 18 |
| Fe (ppm) | 53 | 56 | 58 | 10 |

EXAMPLE 3a

Recrystallization in Acetonitrile

The crude DATPE (200 g; IIIa) was dissolved in acetonitrile (400 ml) at 75° C. The solution was cooled to 20° C. and the crystals of DATPE were filtered and dried under vacuum (~1 mm Hg) at 100° C. The dry DATPE (65 g; IIIb) sample was analyzed; see Table 7.

The above recrystallization procedure was repeated using the purified product (60 g; IIIb). The dry DATPE (43 g; IIIc) sample was analyzed; see Table 7.

The above recrystallization procedure was repeated using the purified product (60 g; IIIb) and active carbon (6 g). The dry DATPE (40 g; IIId) sample was analyzed; see Table 7.

EXAMPLEL 3b

Distillation of the Crude DATPE—Stability Tests

A sample of the crude DATPE (100 g; IIIa) and varying amounts and types of ground bases were introduced into a flask. It was then evacuated and maintained under the specified vacuum conditions during the experiment. The flask was heated to 290° C. for the specified time, then cooled to ambient temperature and analyzed—see Table 8.

TABLE 8

Stability test
The Compound: 1,4-Bis (4-aminophenoxy) - benzene (DATPE)

| Sample | Base Type | Weight g | Temp. °C. | Vacuum mm Hg | -DATPE (% by HPLC) | | | |
|---|---|---|---|---|---|---|---|---|
| | | | | | 0 hrs | 1 hr | 4 hrs | 8 hrs |
| IIIa | — | — | 25 | 760 | 93.0 | 93.0 | 93.0 | 93.0 |
| IIIa-1 | — | — | 290 | 1–5 | 93.0 | 90.8 | 78.6 | 69.6 |
| IIIa-2 | NaOH | 2 | 290 | 1–5 | 93.0 | 91.0 | 81.6 | 72.2 |
| IIIa-3 | NaOH | 8 | 290 | 1–5 | 93.0 | 91.6 | 90.3 | 89.9 |

EXAMPLE 3c

Distillation of the Crude DATPE

A sample of the crude DATPE (100 g; IIIa) and varying amounts of ground bases were introduced into a distillation system. It was then evacuated and maintained under the specified temperature and vacuum conditions during the experiment. Fractions of the distilled product were collected and analyzed at the end of the distillation (after cooling completely to ambient temperature)—see Table 9.

TABLE 9

Distillation
The Compound: 1,4-Bis(4-aminophenoxy)-benzene (DATPE)

| Sample | Type of base | Temp. °C. | Vacuum mm Hg | Theor. # | Yld. % | 4,4'-DADPE (%) | | Metals (ppm) | | |
|---|---|---|---|---|---|---|---|---|---|---|
| | | | | | | HPLC | DSC | Cu | Fe | Other |
| IIIa-4 | — | 285 ± 5 | 1–4 | 1 | 82 | 95.4 | — | <0.5 | <0.5 | |
| IIIa-5 | — | 285 ± 5 | 1–4 | 5 | 69 | 96.5 | — | <0.5 | <0.5 | |
| IIIa-6 | NaOH 2 | 285 ± 5 | 1–4 | 1 | 84 | 97.1 | 97.3 | <0.5 | <0.5 | <1.0 Na |
| IIIa-7 | NaOH 8 | 285 ± 5 | 1–4 | 1 | 93 | 97.2 | 97.1 | <0.5 | <0.5 | <1.0 Na |
| IIIa-8 | NaOH 8 | 285 ± 5 | 1–4 | 5 | 97 | 99.6 | 99.4 | <0.5 | <0.5 | <1.0 Na |
| IIIa-9 | KOH 4 | 285 ± 5 | 1–4 | 5 | 95 | 99.4 | 99.6 | <0.5 | <0.5 | <1.0 K |
| IIIa-10 | KOH 5 | 285 ± 5 | 1–4 | 10 | 98 | 99.9 | 99.9 | <0.5 | <0.5 | <1.0 K |

EXAMPLE 4

Reduction of 5(6)-Nitro-1-nitrophenyl)-1,3,3-trimethylindane (DNPI)

The reduction of the mixture of 5(6)-Nitro-1-(4-nitrophenyl)-1,3,3-trimethylindane (DNPI) (14.5 Kg; IVa) obtained after drying under vacuum (~30 mm Hg) at 80° C. The purity of the sample was analyzed by HPLC (High performance liquid chromatography) and AA (Atomic absorption) analyses, the results of which are summarized in Table 10. The sample was split into portions for further tests as follows:

TABLE 10

| The Compound: 5(6)-Amino-1-(4-aminophenyl)-1,3,3-trimethylindane (DAPI) | |
|---|---|
| | IVa |
| HPLC (Calibrated) DAPI (% wt) | 82.0 |
| DSC DAPI (% wt) | — |
| A.A. | |
| Cu (ppm) | — |
| Fe (ppm) | 1154 |

EXAMPLE 4a

Distillation of the Crude DAPI—Stability Tests

Samples of the crude DAPI (100 g; IVa) with varying amounts and types of ground bases were introduced into parallel flasks. Each flask was then evacuated and maintained under the specified vacuum during the experiment. The flasks were heated to 250° C. for the specified time, then cooled to ambient temperature and analyzed—see Table 11.

TABLE 11

Stability test
The Compound:
5(6)-Amino-1-(4-aminophenyl)-1,3,3-trimethylindane (DAPI)

| Sample | Base Type | Weight g | Temp. °C. | Vacuum mm Hg | 4,4'-DATPE (% by HPLC) 0 hrs | 1 hr | 4 hrs | 8 hrs |
|---|---|---|---|---|---|---|---|---|
| IVa | — | — | 25 | 760 | 82.0 | 82.0 | 82.0 | — |
| IVa-1 | — | — | 250 | 50–70 | 82.0 | 67.3 | 35.4 | — |
| IVa-2 | NaOH | 3 | 250 | 50–70 | 82.0 | 81.2 | 81.0 | — |
| IVa-3 | KOH | 4 | 250 | 50–70 | 82.0 | 81.9 | 82.2 | — |

EXAMPLE 4b

Distillation of the Crude DAPI

A sample of the crude DAPI (100 g; IVa) and varying amounts of ground bases were introduced into a distillation system. It was then evacuated and maintained under the specified temperature and vacuum conditions during the experiment. Fractions of the distilled product were collected and analyzed at the end of the distillation (after cooling completely to ambient temperature)—see Table 12.

TABLE 12

Distillation
The Compound: 5(6)-Amino-1-(4-aminophenyl)-1,3,3-trimethylindane (DAPI)

| Sample | Type of base | Temp. °C. | Vacuum mm Hg | Theor. Plates # | Yld. % | 4,4'-DADPE (%) HPLC | DSC | Metals (ppm) Cu | Fe | Other |
|---|---|---|---|---|---|---|---|---|---|---|
| IVa-4 | — | 215 ± 5 | 0.5–1 | 1 | 21 | — | — | <0.5 | <0.5 | |
| IVa-5 | — | 215 ± 5 | 0.5–1 | 5 | 16 | — | — | <0.5 | <0.5 | |
| IVa-6 | NaOH 4 | 215 ± 5 | 0.5–1 | 1 | 91 | 92.0 | — | <0.5 | <0.5 | <1.0 Na |
| IVa-7 | NaOH 4 | 215 ± 5 | 0.5–1 | 5 | 94 | 98.2 | — | <0.5 | <0.5 | <1.0 Na |
| IVa-8 | NaOH 4 | 215 ± 5 | 0.5–1 | 10 | 96 | 99.6 | — | <0.5 | <0.5 | <1.0 Na |

The advantages of the invention are again demonstrated.

The above description and examples have been given for the purpose of illustration and are not intended to limit the invention. Many modifications can be effected in the various procedures, and many different compounds and reagents employed, all without exceeding the scope of the invention.

We claim:

1. A process for the purification of a crude diaminodiphenyl compound of the structure:

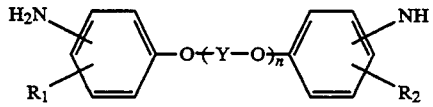

wherein:

$R_1$ and $R_2$ are H, $CH_3$, $C_2H_5$, $C_3H_7$, $C_4H_9$ or

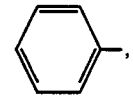

Y is $C(CH_3)_2$,

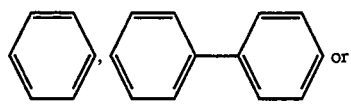 or

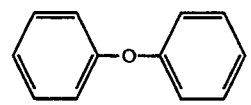

and n=0 or 1 in which the crude product is distilled under vacuum in one step in the presence of at least one alkaline metal base, wherein the distillation temperature is in the range between the melting point of the respective diaminodiphenyl-compound and about 400° C., the pressure is in the range 0.1–400 mm Hg and is maintained at a level at which sublimation of the diaminodiphenyl compound does not occur, and wherein distillation is carried out in the substantial absence of oxygen or ambient air.

2. A process according to claim 1, in which the cation of the base is selected from the group consisting of $Na^+$, $K^+$ and mixtures thereof.

3. A process according to claim 2, wherein the base is selected from the group consisting of NaOH, KOH, $NaHCO_3$, $Na_2CO_3$, $KHCO_3$ and $K_2CO_3$.

4. A process according to claim 3, wherein the molar ratio of the base to the diaminodiphenyl-compound is in the range of from 0.01 to 0.1.

5. A process according to claim 2, wherein the molar ratio of the base to the diaminodiphenyl-compound is in the range of 0.01 to 0.1.

6. A process according to claim 1, wherein the base is selected from the group consisting of $Ca(OH)_2$, $Mg(OH)_2$, $Al(OH)_3$, NaOH, KOH, $NaHCO_3$, $Na_2CO_3$, $KHCO_3$ and $K_2CO_3$.

7. A process according to claim 6, wherein the molar ratio of the base to the diaminodiphenyl-compound is in the range of from 0.01 to 0.1.

8. A process according to claim 1, wherein the molar ratio of the base to the diaminodiphenyl-compound is in the range of from 0.01 to 0.1.

9. A process according to claim 1, wherein the diaminodiphenyl compound is selected from the group consisting of 4,4'-diaminodiphenyl ether, 4,4'-diamino-3-methyldiphenyl ether, and 1,4-bis(4-aminophenoxy)benzene.

* * * * *